United States Patent [19]

Bounds et al.

[11] Patent Number: 5,278,331
[45] Date of Patent: Jan. 11, 1994

[54] WASTE TREATMENT IN DIALKYL PHOSPHOROCHLORIDOTHIOATE PRODUCTION

[75] Inventors: Charles T. Bounds; Gary D. Focht, both of Magnolia, Ark.; W. Brian Harrod, Minden, La.

[73] Assignee: Ethyl Corporation, Richmond, Va.

[21] Appl. No.: 594,404

[22] Filed: Oct. 9, 1990

[51] Int. Cl.⁵ .............................................. C07F 9/20
[52] U.S. Cl. ...................................... 558/148; 558/146
[58] Field of Search .............................. 558/146, 148

[56] References Cited

U.S. PATENT DOCUMENTS

| | | | |
|---|---|---|---|
| 3,089,890 | 5/1963 | Chupp et al. | 260/461 |
| 3,356,774 | 12/1967 | Niermann et al. | 260/981 |
| 3,502,750 | 3/1970 | Anglaret et al. | 260/986 |
| 3,836,610 | 9/1974 | Diveley | 260/986 |
| 3,856,898 | 12/1974 | Diveley | 260/990 |
| 3,897,523 | 7/1975 | Sorstokke | 260/986 |
| 4,024,189 | 5/1977 | Davis | 260/585 A |
| 4,025,586 | 5/1977 | Lippman | 260/986 |
| 4,159,289 | 6/1979 | Anderson et al. | 260/990 |
| 4,356,130 | 10/1982 | Carron et al. | 558/148 |

OTHER PUBLICATIONS

Becke-Goehring, et al., "Topics in Phosphorus Chemistry", vol. 8, Interscience, New York (1976).
Gallagher, et al., "Topics in Stereochemistry", vol. 3, pp. 31-34, Interscience, New York (1968).
Paddock, N. L. "Structure and Reactions in Phosphorus Chemistry", Royal Institute of Chemistry Lecture Series No. 2 (1962).
van Wazer, J., "Phosphorus and Its Compounds: vol. I: Chemistry", Interscience, New York (1958).

Primary Examiner—Mary C. Lee
Assistant Examiner—Michael G. Ambrose
Attorney, Agent, or Firm—Richard J. Hammond; Richard L. Hansen

[57] ABSTRACT

An improvement in the process for making a dialkyl phosphorochloridothioate from $P_2S_5$, alkyl alcohol and chlorine in which the desired product is separated from the reaction mixture by distillation, leaving an unstable, acidic residue, wherein the residue is stabilized and neutralized by reaction with an organic base, thereby enhancing the value of the residue while avoiding potential environmental damage caused by disposal of the residue.

10 Claims, 1 Drawing Sheet

WASTE TREATMENT IN DIALKYL PHOSPHOROCHLORIDOTHIOATE PRODUCTION

This invention is in the field of chemical processes. More specifically, the invention is directed to an improvement in a process for preparing dialkyl phosphorochloridothioates by which the stability and value of certain by-products are enhanced.

BACKGROUND

Diethyl thiophosphoryl chloride and dimethyl thiophosporyl chloride are intermediates in the synthesis of the insecticides parathion and methyl parathion, respectively. Thus, the manufacture of these intermediates has been of great commercial interest, and a number of process innovations have been disclosed. The routes to dialkyl phosphorochloridothioates include both one-step and two-step processes. Phosphorous pentasulfide, alkyl alcohol and chlorine generally are the starting materials for both types of process. The overall reaction can be represented:

$$P_2S_5 + 4ROH + 2Cl_2 \longrightarrow$$

$$2(RO)_2\overset{\underset{\parallel}{S}}{P}-Cl + H_2S + 2HCl + 2S$$

in which R is an alkyl group.

In the one-step process, phosphorus pentasulfide, alcohol and chlorine are reacted together to prepare the ester corresponding to the alcohol, and then the solvent is removed and the product separated. Typical one-step processes are disclosed in U. S. Pat. Nos. 3,356,774 and 3,502,750.

U.S. Pat. No. 3,356,774 discloses reacting a phosphorous pentasulfide suspension in an inert solvent at a temperature within the range of about 0° C. to about 150° C. with chlorine and an alcohol having 1–6 carbon atoms. In this process a stream of chlorine is introduced into the suspension, and the alcohol is added dropwise concurrently. When the chlorination reaction has proceeded to completion, the solvent is removed, and the dialkyl phosphorochloridothioate is recovered by distillation.

According to U.S. Pat. No. 3,502,750 lower alkyl esters of phosphorochloridothioic acid are prepared by reacting chlorine with a lower alkyl ester of dithiophosphoric acid and eliminating the harmful sulfur monochloride by-product from the reaction mixture by reacting it with hydrogen sulfide. The hydrogen sulfide preferably is that produced during production of the dithiophosphoric acid ester. The desired product is recovered by distillation.

According to the two-step process, in the first step, phosphorus pentasulfide is reacted with an alcohol, e.g., ethanol, to produce a dialkyl dithiophosphoric acid, e.g., diethyl dithiophosphoric acid, and hydrogen sulfide. In the second process step, the dialkyl dithiophosphoric acid is chlorinated in an appropriate solvent, such as toluene, with chlorine gas. The product is a dialkyl thiophosphoric acid chloride. The two-step process is described in U. S. Pat. Nos. 3,836,610 and 3,856,898, for example.

According to U.S. Pat. No. 3,836,610 the dialkyl dithiophosphoric acid intermediate is chlorinated, and the reaction mixture is then held at a temperature in the range of 85° C. to 110° C. until it is substantially free of sulfur monochloride, and the sulfur which is produced thereby becomes more thermally stable. The dialkyl thiophosphoryl chloride can then be readily and safely recovered from the reaction mixture by distillation.

According to U.S. Pat. No. 3,856,898 a mixture of a di($C_1$–$C_8$ alkyl) dithiophosphoric acid and amorphous sulfur, which can be present at up to about ⅓ the weight of the acids, is reacted with chlorine. The reaction mixture then is heated to a temperature at which substantially all of the sulfur goes into solution, but the dialkyl phosphorochloridothioate does not decompose. The reaction mixture is then cooled to a temperature at which the dissolved sulfur crystallizes from solution. The crystallized sulfur is then separated from the reaction mixture by filtration, centrifuge, or the like. The supernatant liquid containing the dialkyl phosphorochloridothioate is then distilled.

Prior art which discloses techniques for recovering the desired dialkyl phosphorochloridothioate from the reaction mixture also includes U.S. Pat. No. 3,897,523, which describes a process in which the crude dialkyl phosphorochloridothioate is vaporized in a film evaporator, the vapor is condensed, washed with water at 10° C. to 50° C., and the organic and aqueous phases are separated. The organic phase, which contains the desired dialkyl phosphorochloridothioate, is then dried. U.S. Pat. No. 4,025,586 discloses distilling the dialkyl phosphorochloridothioate product and washing the distillation residue with water to hydrolyze impurities. The washed residue, containing bis(thiophosphine)-sulfide, is then dried and recycled to the chlorination step. U.S. Pat. No. 3,089,890 discloses treating the crude distilled dialkyl phosphorochloridothioate with water, separating the organic phase, and drying it, which leads to the recovery of substantially contaminant-free phosphorochloridothioate. U.S. Pat. No. 4,159,289 describes a process for removing sulfur impurities from dialkyl phosphorochloridothioates by distillation in the presence of a naphthalenic liquid hydrocarbon, which solubilizes or suspends the sulfur.

In the conventional processes for producing dialkyl phosphorochloridothioates various impurities are produced, and the desired thioates generally are separated from the impurities by distillation. Distillation of the reaction mixture leaves a residual, still bottoms material which contains unstable phosphorus compounds, acids, and organic high boilers.

Although treating the still bottoms residue with aqueous strong base is a convenient technique for neutralizing, stabilizing and phase-separating the acidic and phosphorus- containing by-products from the organic high boilers, the aqueous phase still carries substantial quantities of phosphorus- containing materials. These include, for example, alkoxylated derivatives of the salts of hypophosphorous acid ($H_3PO_2$), phosphorous acid ($H_3PO_2$), phosphorous acid ($H_3PO_3$), metaphosphorous acid ($HPO_2$), hypophosphoric acid ($H_2PO_3$), phosphoric acid ($H_3PO_4$), metaphosphoric acid ($HPO_3$), and pyrophosphoric acid ($H_4P_2O_7$), as well as sulfur-containing analogs thereof in which one or more of the oxygen atoms is replaced with sulfur. Deep well injection can be used to dispose of the aqueous phase, but this is costly and potentially damaging to the environment. Furthermore, no value is realized from these by-products when they are simply discarded. The organic high boiler phase, on the other hand, can be utilized as fuel.

SUMMARY OF THE INVENTION

Thus, it is one object of this invention to provide a process whereby acidic and unstable phosphorus-containing by-products which remain as bottoms after distillation of the desired dialkyl phosphorochloridothioate from the reaction mixture are neutralized and stabilized without adding water. It is yet another objective to realize value from such by-products, e.g., by utilizing them as fuel.

In attaining the aforesaid objectives, the invention provides an improvement in the process for reacting phosphorous pentasulfide, alkyl alcohol and chlorine to produce a desired dialkyl phosphorochloridothioate, together with acidic and/or unstable, phosphorus-containing by-products which remain as a still bottoms residue after recovering the dialkyl phosphorochloridothioate by distillation. The improvement comprises treating the residue with organic amine, the result of which is that the acidic and phosphorus-containing by-products remain as part of the single phase from which value can be recovered, e.g., as fuel. In a preferred embodiment, the amine itself is a still bottoms residue from another process.

DETAILED DESCRIPTION

Figure 1:
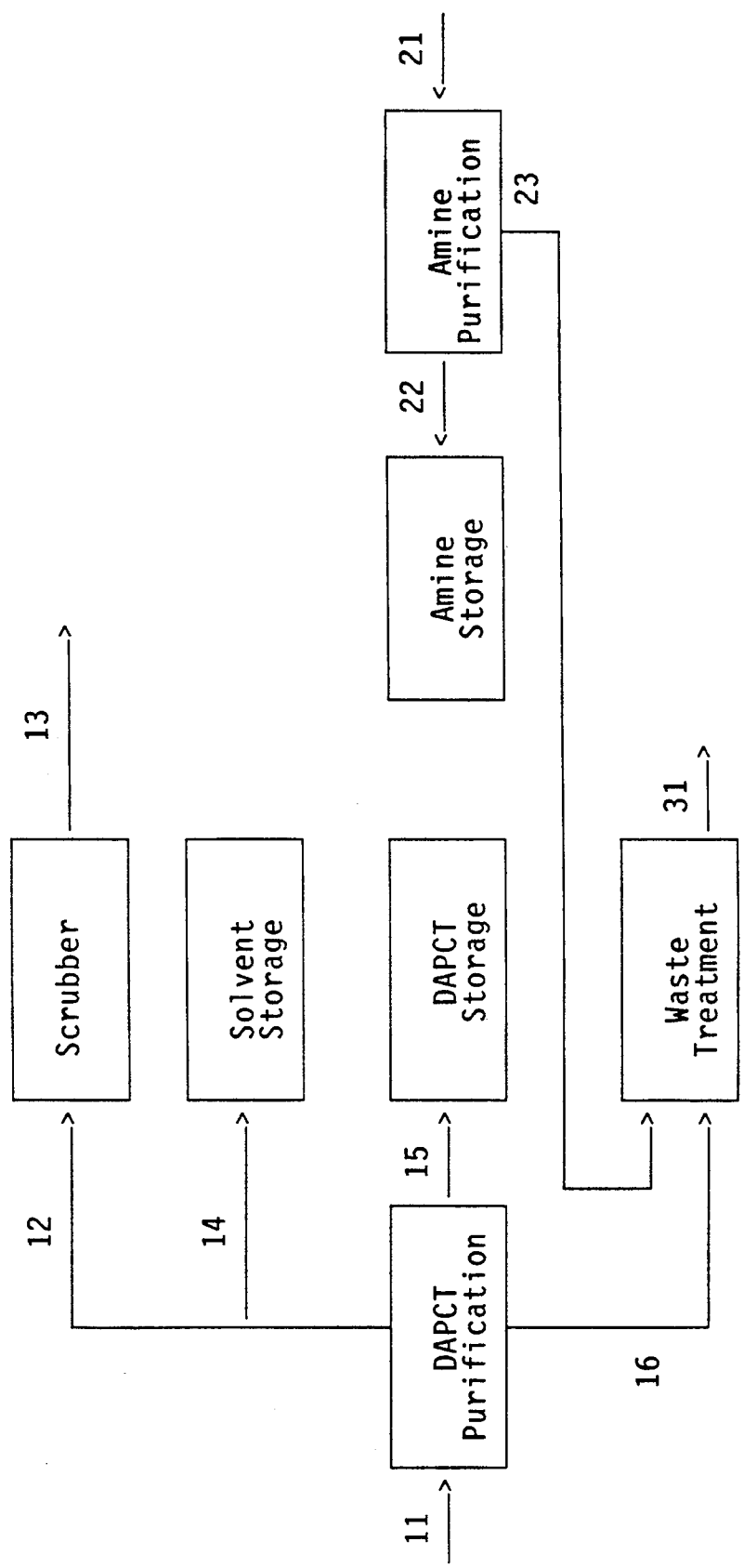
FIG. 1 is a flow diagram illustrating a preferred embodiment of the invention.

This invention is applicable and beneficial to the treatment of waste by-products from the production of dialkyl phosphorochloridothioates, regardless of the details of their production, so long as recovery of the dialkyl phosphorochloridothioate is effected by distillation. For example, the reaction mixture from which the dialkyl phosphorochloridothioate is recovered may be that which arises by practicing the process of U.S. Pat. No. 3,836,610, for example. Alternatively, it may be the product which results by practicing the process of U.S. Pat. No. 3,356,774, for example. In either case, distillation is employed to recover the desired dialkyl phosphorochloridothioate from the reaction mixture, leaving a residue which contains high boiling organic materials, acids, and phosphorus-containing by-products. More specifically, the following materials have been found in such a residue: toluene, sulfur, methyl naphthalenes, $(EtO)_2P(S)Cl$, $EtOP(O)Cl_2$, $(EtO)_3PS$, $(EtO)_2P(O)Cl$, $(EtS)(EtO)P(O)Cl$, $(EtS)(EtO)_2PO$, $C_{30}$ to $C_{40}$ hydrocarbons, $Et_2S_3$, $Et_2S_4$ and $Et_2S_x$, $(EtO)_2P(S)SS(S)P(OEt)_2$, $(EtO)_2P(S)H$, $(EtO)(EtS)P(S)H$, P-O-P tars, EtSH, and Fe compounds.

According to the instant invention, the viscous, oily still bottoms remaining from the distillation are treated with an organic base, stabilizing and neutralizing the still bottoms residue. Amines are a preferred organic base to employ. Among the amines which can be used, lipophilic amines, especially tertiary amines, such as alkyldimethyl or dimethylalkyl amines are advantageously utilized, and such amines in which the alkyl groups, in the aggregate, contain about 10–14 carbon atoms are especially useful. 1-dodecyldimethyl amine is exemplary of such amines.

Organic base at least equivalent to the acid in the residue should be added with efficient mixing. An exothermic reaction is typically observed as the organic base is added. When an aqueous extract of the reaction mixture is basic, not only has the acid been neutralized, but the residue has been stabilized, making the residue, which constitutes a single phase, suitable for use as a fuel.

With reference now to FIG. 1, stream 11 is the reaction mixture which results from the preparation of a dialkyl phosphorochloridothioate from which the sulfur by-product has already been removed. In addition to the desired dialkyl phosphorochloridothioate, stream 11 contains a solvent, such as benzene or toluene, as well as acidic by-products, such as alkoxy and thioalkyl derivatives of the various phosphorus-containing acids and other, structurally more complex phosphorus-containing compounds, in addition to dissolved $H_2S$, HCl, etc. Stream 11 is fed into a distillation assembly or still where the reaction mixture is heated. As the temperature of the reaction mixture increases, dissolved gases, such as $H_2S$ and HCl are taken off first as stream 12; these gases are removed in a scrubber, the remainder being vented as stream 13. The next product recovered overhead is generally the solvent, stream 14, which is stored for reuse. The dialkyl phosphorochloridothioate is then recovered overhead as stream 15. The viscous still bottoms residue, stream 16, is led to a stirred vessel in which it is treated with an organic base, stream 23, at a temperature which generally may range from ambient to about 200° F. The neutralized, stabilized residue, stream 31, can be utilized as, for example, fuel. It will be evident the overall scheme can be adapted for either a batch or continuous process.

In a preferred embodiment, stream 23, the organic base, is organic amine. The organic amine may constitute the still bottoms which remain when a crude amine-containing mixture, stream 21, is distilled to recover the desired amine product as stream 22. For example, U.S. Pat. No. 4,024,189 describes a process for making alkyl amines from an olefin feed. The still bottoms which remain after distilling the desired amine product are suitable for use as the organic base, stream 23. In this way, combining the still bottoms from both processes, which ordinarily gives rise to disposal problems, leads to an environmentally acceptable and profitable solution when the bottoms are combined. Reference to the following Example will clarify the invention.

Example

A reaction mixture derived from the preparation of diethyl phosphorochloridothioate in toluene using a two-step process, and from which the elemental sulfur by-product has been removed, is fed into a still. The reaction mixture is heated under atmospheric pressure, and dissolved gases as well as toluene are recovered overhead, followed by the diethyl phosphorochloridothioate. The bottoms residue is a viscous, oily liquid, the $P^{31}$nmr spectrum of which is consistent with the presence of a number of phosphorus-containing components as shown in Table 1. The nmr chemical shifts measured in $CDCl_3$ are relative to that of 85% $H_3PO_4$ which is assigned a chemical shift of 0.0 ppm. The relative amounts of the components are in area %, which are determined by integrating the areas under the peaks in the nmr spectra.

TABLE 1

| Component | Relative Concentration | $P^{31}$nmr Chemical Shift (ppm) |
|---|---|---|
| 1 | 12.8 | 93–97 |

TABLE 1-continued

| Component | Relative Concentration | $P^{31}$nmr Chemical Shift (ppm) |
|---|---|---|
| 2 | 5.0 | 82–87 |
| 4[a] | 0.3 | 68.5 |
| 6 | 17.6 | 50–55 |
| 8 | 13.7 | 30–40 |
| 9 | 2.4 | 28 |
| 10 | 16.6 | 18–20 |
| 12 | 4.17 | 6 |
| 14 | 6.5 | −15 |

[a]Diethyl phosphorochloridothioate

To the viscous, oily still bottoms are added the bottoms from a process for the production of alkyl dimethyl amines from long chain ($C_8$–$C_{18}$) olefins as described in U.S. Pat. No. 4,024,189. Vapor phase chromatography indicates that the amine-containing bottoms included 28 weight percent olefins, 26 weight percent $C_{12}$ alkyldimethyl amines, and 30 weight percent dialkylmethyl amines. Upon adding the amine-containing bottoms to the phosphorus-containing bottoms an exothermic reaction is observed. The amine-containing bottoms are added in an amount such that the ratio of amine-containing/phosphorus-containing bottoms is about 1:2 v/v. After reacting for about 12 hours at about 25° C., an aqueous extract of the reaction mixture is basic, and the $P^{31}$nmr spectrum of the mixture indicates that several of the phosphorus- containing components have disappeared, and that several others are produced, as shown in Table 2.

TABLE 2

| Component | Relative Concentration | $P^{31}$nmr Chemical Shift (ppm) |
|---|---|---|
| 1 | 11.7 | 93–97 |
| 2[a] | 0.0 | |
| 3[b] | 1.2 | 73–75 |
| 4[a] | 0.0 | |
| 5[b] | 6.6 | 58 |
| 6 | 16.7 | 50–55 |
| 7[b] | 8.8 | 43–47 |
| 8[a] | 0.0 | |
| 9[a] | 0.0 | |
| 10 | 11.9 | 18–20 |
| 11[b] | 8.5 | 8 |
| 12 | <3 | 6 |
| 13[b] | 2.9 | 0 |
| 14 | 18.8 (4 peaks) | 15 |

[a]Disappeared
[b]Produced

It will be evident that this invention is broader than the specific embodiments exemplified herein and that the scope of the invention must be as set forth in the following claims:

We claim:

1. In a process for reacting $P_2S_5$, alkyl alcohol and chlorine to produce a desired dialkyl phosphorochloridothioate which is recovered by distillation, leaving a bottoms residue containing acidic and unstable phosphorus-containing compounds, the improvement therein which comprises treating said bottoms residue with an organic base to stabilize, neutralize and increase the value of said bottoms residue, while also avoiding potential damage to the environment from its disposal.

2. The process of claim 1 wherein said organic base comprises at least one organic amine.

3. The process of claim 2 wherein said organic amine includes tertiary amines selected from the group consisting of alkyldimethyl amine and dialkylmethyl amine.

4. The process of claim 3 wherein alkyl and dialkyl contain about 10–14 carbon atoms.

5. The process of claim 2 wherein said organic amine includes 1-dodecyldimethyl amine.

6. The process of claim 2 wherein said amine is contained in the still bottoms resulting from a process for preparing amines which separates the product from the reaction mixture by distillation, and said organic base comprises said still bottoms.

7. The process of claim 1 wherein said bottoms residue is treated with said organic base at one or more temperatures in the range ambient to about 200° F.

8. The process of claim 1 wherein said bottoms residue is treated with organic base sufficient to make an aqueous extract of the reaction mixture basic.

9. The process of claim 6 wherein about one volume of said amine-containing still bottoms are employed to treat two volumes of said bottoms residue.

10. The process of claim 9 carried out at a temperature of about 25° C. for about 12 hours.

* * * * *